United States Patent [19]

Lionelle et al.

[11] E Patent Number: Re. 32,909

[45] Reissued Date of Patent: Apr. 18, 1989

[54] METAL OXYCARBOXYLATES AND METHOD OF MAKING SAME

[75] Inventors: Joseph E. Lionelle; Jeffrey A. Staffa, both of Salida, Colo.

[73] Assignee: BioSystems Research Inc., Salida, Colo.

[21] Appl. No.: 621,859

[22] Filed: Jun. 18, 1984

Related U.S. Patent Documents

Reissue of:

[64] Patent No.: 4,404,146
Issued: Sep. 13, 1983
Appl. No.: 304,305
Filed: Sep. 21, 1981

U.S. Applications:

[63] Continuation-in-part of Ser. No. 217,119, Dec. 17, 1980, abandoned, which is a continuation-in-part of Ser. No. 194,849, Oct. 7, 1980, abandoned.

[51] Int. Cl.[4] ..... C07F 3/06

[52] U.S. Cl. ..... 556/131; 556/49; 556/61; 556/147; 71/97; 514/492; 514/494; 514/496; 514/501; 514/502; 514/505

[58] Field of Search ..... 260/438.5 R, 429 R, 260/439 R, 431

[56] References Cited

U.S. PATENT DOCUMENTS

| | | |
|---|---|---|
| 2,395,307 | 2/1946 | Weber et al. . |
| 2,661,360 | 12/1953 | Greenspan . |
| 2,873,289 | 2/1959 | MacKellar . |
| 3,133,942 | 5/1964 | Hahl . |
| 3,243,447 | 3/1966 | Rinse . |
| 3,246,024 | 4/1966 | Gwynn et al. . |
| 3,322,800 | 5/1967 | Tideswell . |
| 3,459,677 | 8/1969 | Robeson . |
| 3,576,762 | 4/1971 | Maquet-Martin . |
| 3,647,835 | 3/1972 | Butter . |
| 3,854,923 | 12/1974 | Ott . |
| 3,957,598 | 5/1976 | Merke . |
| 4,172,841 | 10/1979 | Danna et al. . |

FOREIGN PATENT DOCUMENTS

| | | |
|---|---|---|
| 2239615 | 2/1973 | Fed. Rep. of Germany . |
| 2285 | 1/1964 | France . |
| 1483233 | 4/1967 | France . |
| 7192 | of 1897 | United Kingdom . |

OTHER PUBLICATIONS

Catterick et al, Adv. Inorg. Chem & Radiochem. V20, pp. 296–307, 317–324, 330, 334–337, 341–351 (1977).

*Chemical Abstracts,* 83, No. 8, Aug. 25, 1975, p. 91, abstract 70093V.

*Journal of Inorganic Nuclear Chemistry,* 39, 1977, pp. 2139–2141, Cardwell et al.

*Chemical Abstracts,* 56, No. 9, Apr. 30, 1962, p. 9679.

*Chemical Abstracts,* 57, No. 8, Oct. 15, 1962, p. 9434.

*Nature,* vol. 163, No. 4136, Feb. 5, 1949, pp. 225–226.

*Recueil Des Travaux Chimiques Des Pays Bas,* vol. 88, No. 5, May 1969, pp. 545–552.

*Chemical Abstracts,* 90, No. 9, Feb. 26, 1979, p. 442, abstract 90:71236a.

*Chemical Abstracts,* 82, No. 10, Mar. 10, 1975, p. 712, abstract 67569d.

*Chemical Abstracts,* 77, No. 18, Oct. 30, 1972, p. 440, abstract 120504d.

*Journal of the Chemical Society,* Dalton Transaction, 1977, pp. 1420–1425.

*Journal of the Chemical Society,* (A), 1966, No. 12, pp. 1656–1663.

*Journal of the Chemical Society,* (A), 1969, pp. 2270–2273.

*Bulletin of the Chemical Society of Japan,* vol. 27, 1954, No. 2, pp. 112–114.

Catton et al., Advanced Inorganic Chemistry, 3rd Edition, Interscience, N.Y., p. 212, (1972).

*Primary Examiner*—Helen M. S. Sneed
*Attorney, Agent, or Firm*—Larson and Taylor

[57] ABSTRACT

Metal oxycarboxylates are made by reacting a metal, a carboxylic acid, and hydrogen peroxide in aqueous reaction mixture. The metal oxycarboxylate is precipitated and removed from the reaction mixture in high yield and with high purity. The compound is effective in supplying the metal to plants, animals and humans.

17 Claims, No Drawings

METAL OXYCARBOXYLATES AND METHOD OF MAKING SAME

Matter enclosed in heavy brackets [ ] appears in the original patent but forms no part of this reissue specification; matter printed in italics indicates the additions made by reissue.

This application is a continuation in part of Ser. No. 217,119 filed Dec. 17, 1980, now abandoned which is a continuation-in-part of Ser. No. 194,849, filed Oct. 7, 1980 now abandoned.

This application is an application for reissue of U.S. Pat. No. 4,404,146, issued on Sept. 13, 1983.

BACKGROUND OF THE INVENTION

The invention relates to a method of making metal oxyalkylates and to uses therefor.

Zinc oxycarboxylates (zinc, hexakis (acetato) oxotetra) having the empirical formula $C_{12}H_{18}O_{13}Zn_4$ and the structural formula $Zn_4O(CH_3CO_2)_6$, has been described in the literature. See The Bulletin of the Chemical Society of Japan, March 1954, Volume 27, Number 2, pages 112-114. In this literature article, and in others, the compound is prepared by slowly distilling powdered anhydrous zinc acetate in a high vacuum. Zinc oxyacetate sublimes gradually and is collected as a crystalline crust on a cool place in the container. This method is time consuming and expensive.

It is an object of the present invention to provide an efficient and economical process of making zinc and other metal oxycarboxylates. It is a further object of the invention to provide a metal compound which is an effective vehicle for supplying the metal to plants, animals and humans.

BRIEF SUMMARY OF THE INVENTION

The foregoing and other objects which will be apparent to those of ordinary skill in the art are achieved in accordance with the present invention by providing a method for making metal oxycarboxylates which comprises reacting a metal, acetic acid, and hydrogen peroxide in an aqueous reaction mixture, precipitating the metal oxycarboxylate and separating the precipitated metal oxycarboxylate. Preferred metals include beryllium, chromium, manganese, cobalt, nickel, zinc, cadmium and mercury. Mixture or alloys of metals, such as manganese and zinc, may be used. Preferred carboylic acids include aliphatic carboxylic acids containing up to eight carbon atoms, such as formic, acetic, propionic and butyric.

Further in accordance with the invention, the metal oxycarboxylate provides an effective vehicle for supplying the metal to plants, animals and humans. The metal oxycarboxylate is effectively applied to soil for assimilation by plants, and is effectively fed to animals or humans as a food supplement or in food compositions.

DETAILED DESCRIPTION OF THE INVENTION

The metal which is used as a reactant is free metal and is preferably in finely divided form, such as shot or powder, for facilitating reaction. The carboxylic acid is utilized in any convenient concentration, but relatively strong concentrations are preferred because it is preferred that the third reactant, hydrogen peroxide, is added in dilute aqueous solution and because it is preferred to minimize the total amount of water in the reaction mixture. Where the acid is acetic, glacial acid is readily available and readily usable. The amount of acid used is preferably not in excess of stoichiometric. Since it is a relatively simple matter to remove unreacted metal—which remains undissolved—it is preferred to use the metal in an amount in excess of stoichiometric relative to the acid. An excess of about 1.2 to 3 times stoichiometric is preferred.

Hydrogen peroxide is preferably used in excess of stoichiometric. A weight ratio of about 0.1 to 0.5 parts by weight of $H_2O_2$ per part by weight of metal is preferred. The hydrogen peroxide is preferably used in dilute solution of up to 10% $H_2O_2$. A 3% solution is preferable in some situations such as when using glacial acetic acid, since the total amount of water in the aqueous reaction mixture is appropriate when introduced in this manner. The amount of water in the system can vary widely and is preferably at least sufficient to prevent boiling without additional cooling. It is preferred that the amount of water is sufficient to prevent the temperature of the reaction mixture from rising about about 90° C. without additional cooling.

The reaction is preferably carried out at atmospheric pressure for reasons of economy and at temperatures below the boiling point of the reaction mixture. In general, a temperature of from room temperature up to about 130° C. is preferred.

After the reaction is complete, excess metal is preferably removed by filtration or by decantation of the liquid phase. Precipitation is preferably achieved by adding acetone and cooling, but may be effected by careful evaporation of the aqueous reaction mixture. The amount of acetone is preferably about 1-5 volumes per volume of the aqueous phase and the aqueous phase is preferably cooled, or permitted to cool, to at least room temperature before the addition of the acetone in order to minimize evaporation of acetone. The solution is then preferably chilled, preferably to a temperature of less than 50° F., to precipitate the metal oxycarboxylate. While chilling can be carried much lower, it is generally not necessary, in order to precipitate substantially all of the metal oxycarboxylate to cool below about 30° F.

The precipitated metal oxycarboxylate is recovered by filtration or the like and drying.

While the structure of the zinc oxycarboxylate has been confirmed to be $Zn_4O(R—CO_2)_6$, and that of the manganese $Mn_4O$ $(R—CO_2)_6$, wherein R is hydrogen or alkyl, the structure of reaction products of all of the other metals and acids has not yet been confirmed. However, the following general information is attributed.

$$M_xO(R—CO_2)_6$$

where M is a metal, x is an integer of 2 to 8, and R is hydrogen or alkyl.

Examples of the invention follow:

EXAMPLE I

Preparation of Zinc Oxyacetate

Into a 600 milliliter beaker are placed 50 grams (0.765 gram-atoms) of zinc metal shot. Then 45 milliliters (0.767 moles) of glacial acetic acid is added. To this mixture is added 400 milliliters of 3% hydrogen peroxide. This mixture is stirred at room temperature for 1 hour.

The reaction liquid mixture is decanted to remove the unreacted zinc shot. Then 1200 milliliters of acetone is added to the decanted liquid, and the solution is cooled to 40° F. After one hour, the precipitate is filtered to yield 50 grams of white product (Hexakis (acetato) oxotetra zinc).

EXAMPLE II

Preparation of Zinc Oxyacetate

Into a 2000 milliliter beaker is placed 100 grams (1.53 g-atoms) of zinc metal shot. Then 90 milliliters (1.57 moles) of glacial acetic acid is added. To this mixture is added 800 milliliters of 3% hydrogen peroxide. The mixture is heated to 94° C. for 30 minutes with stirring. The unreacted zinc is removed, and the solution is chilled overnight in a larger container after adding 2400 ml acetone to yield 115 grams of white product (hexakis (acetato) oxotetra zinc).

EXAMPLE III

Zinc Fertilizer

This example compares the effectiveness of the compound of Example II (ZTA) with $ZnSO_4$ and zinc ethylene diamine tetraacetic acid (ZnETDA) in a greenhouse study. Parameters measured are dry matter accumulation, plant zinc concentration, plant zinc uptake and residual soil zinc levels. The soil used is a Cozad silt loam, saline-alkali. Analysis shows:

| pH | Salts mmh/cm | % O.M. | Bray 1P ppm | Exch K ppm | Zn | Fe | Cu | Mn | B |
|---|---|---|---|---|---|---|---|---|---|
| | | | | | ppm | | | | |
| 8.4 | 22 | 2.8 | 14 | 1264 | 0.4 | 2.9 | 0.5 | 22 | 0.7 |

This is a slightly saline soil ($EC_e$=2.2 mmho/cm) and would normally show 10–15% yield reductions compared to a similar non-saline soil. The iron level is low and indicates problems with iron chlorosis. This low level of Fe could be a problem when the soil is fertilized with zinc because of possible Fe×Zn interactions. Even though the soil is zinc deficient, the addition of zinc could depress yields due to the low Fe level. This soil shows 6% exchangeable sodium and an SAR of 5. This is sufficient Na to maintain a high pH in this calcareous soil above 8.3. The high pH will accentuate Fe chlorosis problems. Treatments used are:

1. Check-no zinc
2. 4 ppm Zn (soil basis) as ZTA
3. 8 ppm Zn as ZTA
4. 4 ppm Zn as $ZnSO_4$
5. 8 ppm Zn as $ZnSO_4$
6. 4 ppm Zn as ZnEDTA
7. 8 ppm Zn as ZnEDTA Additional fertilizer supplied on a soil basis is 100 ppm N as $NH_4NO_3$ and 30 ppm P as monocalcium phosphate. Another 50 ppm N as $NH_4NO_3$ is added when plants are at the 5-leaf stage. A total of 2.25 kg of soil is weighed out for each pot. Dry soil plus fertilizer is mixed thoroughly in a Twin Shell blender, then placed in plastic bags which are placed inside the pots. Field capacity of the soil is near 28% on a gravimetric basis. Pots are tamped to attain a bulk density near 1.3 g/cm$^3$. Six seeds of Pioneer 3901 corn are planted 1 inch deep on Day 1. Plots are watered to field capacity using deionized-distilled water. The soil is wetted uniformly to the bottom of the pot. Pots are set on the east side of the greenhouse (outdoors). Each pot is placed in a hole so the rim of the pot is ½ inch above the soil surface. This is done to moderate soil heating during the day. Pot weight is checked every 1 to 2 days and pots are watered with deionized distilled water to maintain field capacity.

Plant emergence is highly variable. Stands ranged from 2 to 6 plants/pot. After 2 weeks, more corn is replanted. Pots are thinned to 4 plants per pot at the 4-leaf stage. This later corn does not develop fully so when dry matter is harvested on day 34 only the first-planted plants are taken. Two to four large plants are taken. Corn is in the 7-leaf stage at this time. Plant dry matter accumulation is calculated as grams/plants because of the unequal plant numbers. Dry matter accumulation and statistical analysis are shown in Table 1. Treatments have no effect on dry matter yield. The only observation at harvest is that the 8 ppm Zn level of ZnEDTA seem to have smaller plants than other treatments. The dry weights confirm this. The lack of a zinc response is not surprising in light of the low Fe level. All plants shown moderate visual symptoms of Fe chlorosis.

Zinc content of plants is given in Table 2. Application of zinc significantly increases plant zinc content. The ZTA is equally as effective as $ZnSO_4$. ZnEDTA shows the largest increases in plant zinc.

Zinc uptake is simply dry matter times zinc content. Values are given in Table 3. Zinc uptake is significantly affected by zinc source and rate. ZnEDTA produces the highest levels. ZTA is significantly better than $ZnSO_4$ (average of 4 and 8 ppm levels) at the 7% level of probability.

From the basis of zinc content and zinc uptake, ZTA is equal to or better than $ZnSO_4$.

Residual soil levels of zinc are determined to note reversion of zinc to insoluble forms. DTPA extractable zinc is shown in Table 4.

The surprising fact is the extremely high soil levels of zinc in all samples. This sample initially shows 0.4 ppm DTPA-Zn. After the experiment, the check shows an average of 16.8 ppm Zn. The extreme heat and the high organic matter level could have caused appreciable mineralization of soil zinc. Different results would be expected if this work were done in the field or under cooler temperatures. The 8 ppm level of ZnEDTA is the only treatment showing a significant increase in residual soil zinc. The 4 ppm levels of all sources have little effect on residual soil zinc. This is to be expected since most of the zinc is probably removed by the plants. The 8 ppm levels do show increases above the check. It is difficult to determine the residual Zn effects when the check is so high.

The ZTA increases plant zinc as well as or better than $ZnSO_4$.

TABLE 1

Dry matter accumulation in grams per plant

| Treatment | Replication I | II | III | IV | Avg. |
|---|---|---|---|---|---|
| Check | 1.13 | 1.90 | 1.56 | 1.91 | 1.63 a* |
| 4 ppm ZTA—Zn | 1.74 | 1.17 | 1.43 | 2.07 | 1.60 a |
| 8 ppm ZTA—Zn | 1.67 | 1.74 | 1.92 | 1.49 | 1.70 a |
| 4 ppm $ZnSO_4$—Zn | 1.36 | 1.40 | 1.73 | 1.45 | 1.49 a |
| 8 ppm $ZnSO_4$—Zn | 1.56 | 1.47 | 1.60 | 1.61 | 1.56 a |
| 4 ppm ZnEDTA—Zn | 1.51 | 1.43 | 1.50 | 1.90 | 1.59 a |

TABLE 1-continued

| Dry matter accumulation in grams per plant | | | | | |
|---|---|---|---|---|---|
| | Replication | | | | |
| Treatment | I | II | III | IV | Avg. |
| 8 ppm Zn—EDTA—Zn | 1.50 | 1.46 | 1.39 | 1.21 | 1.39 a |

*Values followed by the same letter are not significantly different at the 5% level.

One-way Analysis of Variance

| Source | df | ss | MS | F |
|---|---|---|---|---|
| Total | 27 | 1.4923 | | |
| Treatment | 6 | 0.2494 | 0.04157 | 0.70 NS |
| Error | 21 | 1.2429 | 0.05919 | |

$$cv = \frac{0.2433}{1.565} = 15.5\%$$

TABLE 2

| Zinc concentration of corn plants | | | | | |
|---|---|---|---|---|---|
| | Replication | | | | |
| Treatment | I | II | III | IV | Avg. |
| | ppm | | | | |
| Check | 75 | 19 | 56 | 37 | 47 a* |
| 4 ppm ZTA—Zn | 156 | 178 | 196 | 142 | 168 b |
| 8 ppm ZTA—Zn | 210 | 248 | 228 | 144 | 208 b |
| 4 ppm $ZnSO_4$—Zn | 156 | 118 | 84 | 118 | 119 ab |
| 8 ppm $ZnSO_4$—Zn | 130 | 162 | 106 | 244 | 161 b |
| 4 ppm ZnEDTA—Zn | 296 | 416 | 446 | 300 | 365 c |
| 8 ppm ZnEDTA—Zn | 836 | 560 | 658 | 576 | 683 d |

*Values followed by the same letter are not significantly different at the 5% level.

One-way Analysis of Variance

| Source | df | ss | MS | F |
|---|---|---|---|---|
| Total | 27 | 1,181,094.107 | | |
| Treatment | 6 | 1,100,713.357 | 184,452.226 | 47.9* |
| Error | 21 | 80,380.750 | 3,827.655 | |

$$cv = \frac{61.868}{249.8} = 24.8\%$$

**Significant at the 1% level.

TABLE 3

| Zinc uptake by corn | | | | | |
|---|---|---|---|---|---|
| | Replication | | | | |
| Treatment | I | II | III | IV | Avg. |
| | micrograms | | | | |
| Check | 85 | 36 | 87 | 71 | 70 a* |
| 4 ppm ZTA—Zn | 271 | 208 | 280 | 294 | 263 bc |
| 8 ppm ATA—Zn | 351 | 432 | 438 | 215 | 359 c |
| 4 ppm $ZnSO_4$—Zn | 212 | 165 | 145 | 171 | 173 b |
| 8 ppm $ZnSO_4$—Zn | 203 | 238 | 170 | 393 | 251 bc |
| 4 ppm ZnEDTA—Zn | 447 | 595 | 669 | 570 | 570 d |
| 8 ppm ZnEDTA—Zn | 1254 | 818 | 915 | 818 | 951 e |

*Values followed by the same letter are not significantly different at the 5% level.

One-way Analysis of Variance

| Source | df | ss | MS | F |
|---|---|---|---|---|
| Total | 27 | 2,352,644.107 | | |
| Treatment | 6 | 2,128,656.357 | 534,776.06 | 33.3** |
| Error | 21 | 223,987.750 | 10,666.08 | |

-continued

| Source | df | ss | MS | F |
|---|---|---|---|---|

$$cv = \frac{103.277}{376.82} = 27.4\%$$

**Significant at the 1% level.

TABLE 4

| DTPA extractable zinc in the soil at the end of the experiment | | | | | |
|---|---|---|---|---|---|
| | Replication | | | | |
| Treatment | I | II | III | IV | Avg. |
| | ppm | | | | |
| Check | 11 | 12 | 34 | 10 | 16.8 a* |
| 4 ppm ZTA—Zn | 18 | 16 | 24 | 20 | 19.5 a |
| 8 ppm ZTA—Zn | 22 | 26 | 22 | 19 | 22.3 a |
| 4 ppm $ZnSO_4$—Zn | 15 | 14 | 19 | 18 | 16.5 a |
| 8 ppm $ZnSO_4$—Zn | 33 | 27 | 22 | 31 | 28.3 ab |
| 4 ppm ZnEDTA | 20 | 18 | 22 | 19 | 19.8 a |
| 8 ppm ZnEDTA | 53 | 39 | 37 | 38 | 41.8 b |

*Values followed by the same letter are not significantly different at the 5% level.

One-way Analysis of Variancee

| Source | df | ss | MS | F |
|---|---|---|---|---|
| Total | 27 | 2,652.964 | | |
| Treatment | 6 | 1,917,214 | 321.202 | 9.29** |
| Error | 21 | 724.750 | 34.5595 | |

$$cv = \frac{5.879}{23.54} = 25.0\%$$

**Significant at the 1% level.

As mentioned above, the metal oxycarboxylate can be added to soil as such or in admixture with a suitable carrier such as a fertilizer composition containing other fertilizer values such as N, P or K. The compound is also suitable for supplying metals to animals or humans and can be supplied in tablet or other convenient form in admixture with a suitable carrier such as a water soluble wax or other solid excipient. The compound can also be admixed with a food product for human or animal consumption, such as breakfast cereal, animal foods, and the like.

EXAMPLE IV

Animal Food Supplement

Zinc oxyacetate is administered to rats by adding it to water consumed by the rats. After a period of time, the rats are sacrificed and zinc concentration in the blood plasma is determined by atomic absorption analysis. Results are given in Table 5.

TABLE 5

| Sample # | Sex | Dose | Day From Dosing | Zn Conc. μg/ml Plasma | Elevation i.e. Minus Control |
|---|---|---|---|---|---|
| a | F | 1.25 g/kg | 9 | 6.45 | 4.3 |
| b | F | 0.156 g/kg | 9 | 3.65 | 1.5 |
| c | F | 0.078 g/kg | 9 | 3.10 | 0.95 |
| d | F | 0.039 g/kg | 9 | 4.25 | 2.1 |
| e | F | 2 g/kg | 7 | 3.80 | 1.65 |
| f | M | 1.25 g/kg | 9 | 3.00 | 0.85 |
| g | M | 0.312 g/kg | 9 | 3.10 | 0.95 |
| h | M | 0.039 g/kg | 9 | 4.25 | 2.1 |
| i | M | 3 g/kg | 7 | 13.85 | 11.7 |
| j | M | 2 g/kg | 7 | 4.75 | 2.6 |
| Control | M | no dose | | 2.15 | |

The amount of compound that is administered will, of course, depend on the amount of zinc which is desired to be added to the plant or ingested by the animal or human. For agricultural use, the amount of zinc which is to be used may be determined by the amount by which the soil is considered deficient in zinc content or by the amount by which the plant is considered deficient in zinc content. Similarly, for animal or human use, the zinc dosage may be determined by a dietary zinc deficiency or by a zinc deficiency in blood plasma, in body tissues, or the like. The dosage can vary widely for a particular metal, particularly for agricultural purposes. For zinc, dosages, in general, would typically be as follows:

| USE | DOSAGE |
|---|---|
| Agricultural | 2-12 ppm in the soil |
| Animal | 50-250 mg. per day |
| Human | 50-150 mg. per day |

EXAMPLES V-XI

Example I is followed except that the zinc metal shot is replaced with 50 grams of the following finely divided metals: V—beryllium; VI—chromium; VII—manganese; VIII—cobalt; IX—nickel; X—cadmium; XI—mercury. The recovered metal oxyacetate reaction products are useful, in the manner indicated above for the zinc oxyacetate reaction product, for supplying the metal to plants, animals, and humans. The amount of the metal to be supplied will, of course, depend on the metal; desirable amounts of each to be supplied are well known for particular applications.

EXAMPLE XII

Example I is followed except that the glacial acetic acid is replaced with an equivalent amount of formic acid. The recovered zinc oxycarboxylate product is useful as indicated above.

EXAMPLE XIII

The compound of Example VII is analyzed and found to have the following structural formula: $Mn_4O(CH_3—CO_2)_6$.

What is claimed is:

1. A method of preparing a metal oxycarboxylate which comprises reacting, in an aqueous reaction mixture at a temperature of below about 130° C., a metal, a carboxylic acid, and hydrogen peroxide to form said metal oxycarboxylate said hydrogen peroxide being utilized in said reaction mixture as a dilute aqueous solution of up to 10% $H_2O$, precipitating said metal oxycarboxylate and separating the precipitated metal oxycarboxylate.

2. A method according to claim 1 wherein said metal comprises zinc.

3. A method according to claim 1 wherein said metal is selected from the group consisting of beryllium, [magnesium,] chromium, manganese, iron, cobalt, nickel, [palladium, platinum, copper, silver, gold,] cadmium and mercury.

4. A method according to claim 1 wherein said carboxylic acid is an aliphatic carboxylic acid containing from 1 to 8 carbon atoms.

5. A method according to claim 4 wherein said acid is selected from the group consisting of formic, acetic, proprionic and butyric acid.

6. A method according to claim 5 wherein said acid comprises acetic acid.

7. A method according to claim 1 wherein the metal oxycarboxylate is precipitated by adding acetone to said reaction mixture.

8. A method according to claim 1 wherein the amount of metal is in excess of stoichiometric and wherein unreacted metal is removed from the reaction mixture prior to precipitation of said metal oxycarboxylate.

9. A method according to claim 1 wherein the amount of hydrogen peroxide is from 0.1 to 0.5 parts by weight per part by weight of metal.

10. A method according to claim 7 wherein the temperature of said reaction mixture is not in excess of about room temperature at the time of the addition of said acetone.

11. A method according to claim 10 wherein the reaction mixture is cooled to a temperature not in excess of 50° F. to facilitate said precipitation.

12. A method according to claim 1 wherein said metal oxycarboxylate has the formula $M_4O(R\text{-}CO_2)_6$.

13. A method according to claim 12 wherein said metal is selected from the group consisting of zinc, manganese, and cobalt.

14. A method according to claim 13 wherein said metal comprises zinc.

15. A method according to claim 12 wherein said metal is selected from the group consisting of beryllium, chromium, nickel, cadmium and mercury.

16. A method according to claims 12 and 13 wherein said carboxylic acid is selected from the group consisting of acetic acid and formic acid.

17. A method according to claim 16 wherein said metal comprises zinc.

[18. Metal oxycarboxylate having the formula $M_4O(R\text{-}CO_2)_6$ wherein M is a metal cation selected from the group consisting of chromium, manganese, cobalt, nickel cadmium, and mercury, and R is hydrogen or alkyl.]

[19. A compound according to claim 18 wherein said metal comprises manganese.]

[20. A compound according to claim 19 wherein R is hydrogen or methyl.]

* * * * *